United States Patent [19]

Ishida et al.

[11] Patent Number: 4,670,403

[45] Date of Patent: Jun. 2, 1987

[54] METHOD OF AMINO ACID ANALYSIS

[75] Inventors: Yasuo Ishida, Mukoh; Michihiko Fujiwara, Kyoto; Toshio Kinoshita, Chigasaki; Noriyuki Nimura, Yokohama, all of Japan

[73] Assignee: Shimadzu Corporation, Kyoto, Japan

[21] Appl. No.: 649,549

[22] Filed: Sep. 11, 1984

[30] Foreign Application Priority Data

Oct. 14, 1983 [JP] Japan .................... 58-193070

[51] Int. Cl.$^4$ .................. G01N 21/77; G01N 33/52; G01N 33/68
[52] U.S. Cl. ........................ 436/90; 436/89; 436/164; 436/172
[58] Field of Search ............ 436/86, 89, 90, 161, 436/172, 176, 164, 174, 177, 178

[56] References Cited

U.S. PATENT DOCUMENTS

| | | | |
|---|---|---|---|
| 3,892,530 | 7/1975 | Felix et al. | 436/90 |
| 3,933,430 | 1/1976 | Hare | 436/90 |
| 4,133,753 | 1/1979 | Takeuchi et al. | 436/89 X |

FOREIGN PATENT DOCUMENTS

| | | | |
|---|---|---|---|
| 2622547 | 11/1977 | Fed. Rep. of Germany | 436/89 |
| 2838760 | 3/1980 | Fed. Rep. of Germany | 436/161 |
| 0135355 | 8/1982 | Japan | 436/89 |
| 0189555 | 11/1983 | Japan | 436/86 |

OTHER PUBLICATIONS

Yasuhara et al, Chemical Abstracts, vol. 100, Abstract No. 100:117357w, Apr. 1984.
Aswad, Anal. Biochem., vol. 137, No. 2, pp. 405–409, Mar. 1984.
Simons et al, Anal. Biochem., vol. 90, pp. 705–725, 1978.
Simons et al, J. Org. Chem., vol. 43, No. 14, pp. 2886–2891, 1978.
Lee et al, J. Bio. Chem., vol. 254, No. 14, pp. 6248–6251, 1979.
Ishida et al, J. of Chromatography, vol. 204, pp. 143–148, 1981.
Aminco Laboratory News, vol. 31, No. 1, pp. 1–2, 1975.
Gardner et al, Anal. Biochem., vol. 101, pp. 61–65, 1980.
Nakamura et al, Chemical Abstracts, vol. 98, No. 98:125304g, 4/11/83.
Aswad, Chemical Abstracts, vol. 100, No. 100:156961h, 5/7/84.
Nakamura et al, Anal. Chem., vol. 53, No. 14, pp. 2190–2193, 1981.

*Primary Examiner*—Barry S. Richman
*Assistant Examiner*—Robert J. Hill, Jr.
*Attorney, Agent, or Firm*—Stiefel, Gross, Kurland & Pavane

[57] ABSTRACT

A method of amino acid analysis by reacting an amino acid-containing sample with o-phthalaldehyde and an N-protective group-substituted cysteine such as N-acetyl-L-cysteine under an alkaline condition to yield a fluorescent compound and measuring the intensity of fluorescence or absorbance of the resulting compound. The method is sensitive for quantitative and qualitative analysis of a secondary amino acid such as proline when it is beforehand subjected to an oxidation.

5 Claims, 11 Drawing Figures

METHOD OF AMINO ACID ANALYSIS

BACKGROUND OF THE INVENTION

1. Field of the Invention

The present invention relates to a method of and an apparatus for amino acid analysis, and more particularly to an analysis method of qualitatively and quantitatively determining various amino acids with ease, the method being adapted to qualitatively and quantitatively determining even imino acids such as proline with high sensitivity.

2. Description of the Prior Art

An amino acid analysis is conducted by a method wherein o-phthalaldehyde (hereinafter referred to as "OPA") and mercaptoethanol are used. With this method, each amino acid separated off by a column is reacted with OPA and mercaptoethanol to form a fluorescent compound as shown below, and the intensity of fluorescence or absorbance of the compound is measured for qualitative or quantitative determination.

When the sample is a secondary amino acid of the imino acid type, such as proline, the sample is reacted with hypochlorous acid or like oxidizer and thereby converted to a primary amino acid, which is then subjected to the above reaction. However, the conventional method is low in analysis sensitivity for proline or like secondary amino acid of the imino acid type even when the acid is reacted after oxidation. The method has another problem in that the mercaptoethanol used releases a foul odor.

To overcome the above problems, we have already proposed a method which is adapted to achieve improved analysis sensitivity for imino acids such as proline by reacting the converted primary amino acid with OPA of increased concentration under optimized conditions in respect of reaction time and temperature (Published Unexamined Japanese Patent Application No. SHO 57-135355).

SUMMARY OF THE INVENTION

The present invention provides a method of amino acid analysis characterized by reacting an amino acid-containing sample with o-phthalaldehyde and an N-protected group-substituted cysteine under an alkaline condition to obtain a fluorescent compound and measuring the intensity of fluorescence or absorbance of the compound.

By the analysis method of the present invention, samples containing imino acids such as proline can be analyzed with high sensitivity (about ten times the sensitivity of the usual method using mercaptoethanol) without the necessity of increasing the concentration of OPA and also without entailing the problem of noxious odor.

When a D,L-mixture of α-amino acids having asymmetric carbon atoms is analyzed as the sample, fluorescent compounds which are diastereomers are formed, so that the compounds can be easily subjected to optical resolution, and the D-acid and the L-acid can be readily determined qualitatively or quantitatively based on the intensities or absorbances of the compounds.

DESCRIPTION OF THE PREFERRED EMBODIMENT

The amino acid containing-sample to be analyzed by the method of the invention means one containing at least one primary amino acid. When containing a secondary amino acid of the imino acid type, the sample is oxidized first with an oxidizer, e.g. hyprochlorous acid (usually in the form of a salt), by the usual method, and is then analyzed. Samples containing a secondary amino acid, such as sarcosine or like N-lower alkylsubstituted glycine, can also be analyzed similarly after oxidation. The oxidation treatment is conducted to convert the secondary amino acid to the primary.

The amino acids contained in the sample to be analyzed by the present method may be optically active acids or racemic modifications. When the sample is a D,L-mixture, especially racemic modification, the diastereomers resulting from reaction are subjected to optical resolution as will be described later, whereby the D-form and L-form can be separated for analysis.

The amino acids to be analyzed include, for example, glycine (Gly), alanine (Ala), Valine (Val), leucine (Leu), isoleucine (Ile), serine (Ser), threonine (Thr), cysteine (Cys), cystine (Cys-Cys), methionine (Met), aspartic acid (Asp), glutamic acid (Glu), arginine (Arg), lysine (Lys), histidine (His), asparagine (Asp-NH$_2$), glutamine (Glu-NH$_2$), phenylalanine (Phe), tyrosine (Tyr), tryptophan (Trp), proline (Pro), hydroxyproline (Hy-Pro), sarcosine etc. Such acids may be in the form of a mixture.

Examples of protective groups in N-protective group-substituted cysteines useful for the present invention are acetyl, trifluoroacetyl, ethoxycarbonyl, ter-butoxycarbonyl, benzyloxycarbonyl, p-nitrobenzyloxycarbonyl, p-nitrophenylsulfonyl, p-toluenesulfonyl and trityl. Among such cysteines, N-acetyl-D- or L-cysteine is preferred.

The N-protective group-substituted cysteines can be prepared by reacting cysteine with an N-protective reagent by a known method, for example, by reacting D- or L-cysteine with a compound, such as acetic anhydride, acetyl chloride, 2-ter-butoxycarbonyloxyimido-2-phenylacetonitrile, N-carboethoxyphthalimide, benzyloxycarbonyl chloride, S-ethyl-thiol-trifluoroacetate, p-nitrocarbobenzoxy chloride, o-nitrophenylsulfonyl chloride, phenyltrifluoroacetate, p-toluenesulfonyl chloride, trityl chloride or the like.

The N-protected-cysteines thus obtained themselves are chiral compounds, and it is usually suitable to use such compounds having high optical purity. Especially when the reaction product is to be subjected to optical resolution, it is preferable to use those having an optical purity of 100%. However, when the post-column method is to be resorted to as will be described later, D,L-mixtures are usable.

The amino acid-containing sample can be reacted with OPA and an N-protective group-substituted cysteine usually under the same conditions as when samples are reacted with OPA and mercaptoethanol by the conventional method, especially under alkaline conditions. For example, OPA and the N-protective group-substituted cysteine are mixed with a buffer having a pH of 9 to 12, preferably about 10 to about 11 to obtain a weakly alkaline reaction reagent, the reagent is mixed with the amino acid-containing sample, and the mixture is suitably heated, whereby the reaction can be carried out readily (usually within several tens of seconds). This reaction of the invention proceeds as represented by the following scheme wherein N-acetyl-L-cysteine is used.

(Sample)                    (Fluorescent compound)

Generally it is suitable to use a buffer of the borate type, carbonate type or borate-carbonate type as the buffer. Examples of such buffers are $H_3BO_3/NaOH$ buffer, $H_3BO_3/KOH$ buffer, $Na_2CO_3/H_3BO_3/K_2SO_4$ buffer, $Na_2CO_3/NaHCO_3$ buffer, etc., of which $H_3BO_3/NaOH$ buffer and $Na_2CO_3/H_3BO_3/K_2SO_4$ buffer are preferable.

For the above reaction, it is suitable to heat the mixture usually at a temperature of 20° to 70° C., preferably 55° to 65° C. Further it is suitable to use the N-protective group-substituted cysteine and o-phthalaldehyde in a mole ratio of 1:1-4.6, preferably 1:1-2.

The fluorescent compound resulting from the reaction of OPA and the N-protective group-substituted cysteine is easily detectable as it is, based on the intensity of fluorescence or absorbance thereof. It is generally desirable to detect the compound based on flurorescence which assures the detection with higher sensitivity. The optimum concentration of the compound for the detection is 0.5 pmol to 1 μmol. Various detectors which are known in the art are usable for detecting the compound.

When a sample containing a plurality of amino acids is to be analyzed, the sample is treated in accordance with the construction of the so-called amino acid analyzer. Thus, it is suitable to feed the sample to a liquid chromatographic column for the separation of amino acids, to successively subject the amino acids to the above reaction and to feed the resulting products to a detector. However, the sample may be subjected to the reaction first, then fed to the liquid chromatographic column for separation and thereafter to the detector. In other words, the amino acids may be converted to fluorescent compounds before separation (pre-column method) or after separation (post-column method).

From the above viewpoint, the present invention provides an amino acid analyzer comprising a buffer channel extending from a feeder for amino acid-containing samples and connected to a separating column, an eluate channel extending from the separating column and connected to a detector having means for measuring the intensity of fluorescence or absorbance, and a mixture reactor provided for the buffer channel (corresponding to the pre-column method) or the eluate channel (corresponding to the post-column method) for accommodating an alkaline buffer solution of o-phthalaldehyde and an N-protective group-substituted cysteine. The analyzer may further comprise a pre-reactor for hypochlorous acid disposed upstream from the mixture reactor.

On the other hand, when a sample containing D,L-amino acids is treated, two kinds of fluorescent compounds are obtained which are represented by the following formulae (I) and (II).

These compounds are in a diastereomeric relationship and can be readily separated by usual liquid chromatography. When the sample has an optical purity of 100%, the reaction produces one of the diastereomers. In this case, there is no particular need for separation.

For the liquid chromatography, concurrent phase, reversed phase or ion-exhange chromatography, for example, can be resorted to. Stated more specifically, silica gel may be used as the static phase, and hexane as the mobile phase, or a cationic exchange resin is usable as the static phase, and a buffer as the mobile phase.

The diastereomers separated by a suitable liquid chromatographic procedure can be directly detected fluorophotometrically or absorptiometrically. The fluorophotometric procedure is usually desirable since the compounds can then be detected with higher sensitivity. Various detectors already known in the art are usable for this purpose.

The method described is usable also for the optical resolution of various amino-containing optical isomers other than amino acids.

The invention will be described in greater detail with reference to the following examples and accompanying drawings.

EXAMPLE 1

Figure 1:
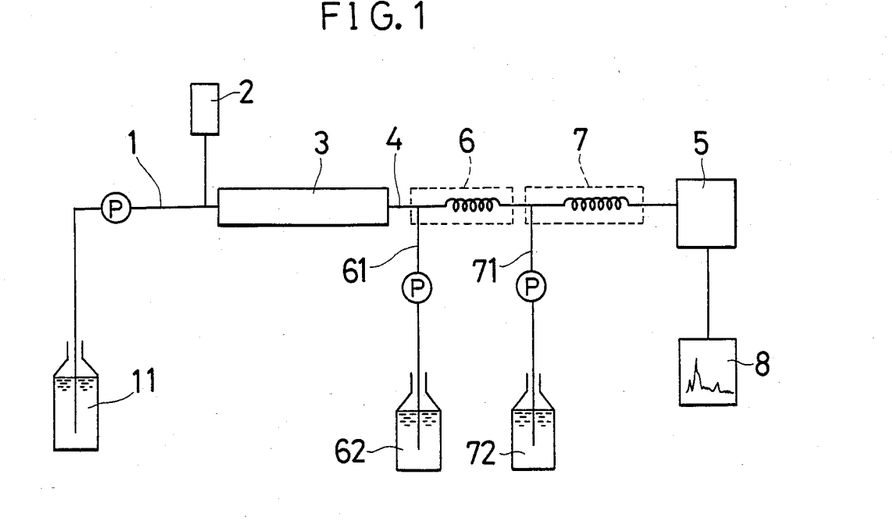
FIG. 1 is a diagram showing an example of apparatus for practicing the amino acid analysis method of the invention.

FIG. 1 is a diagram showing an example of apparatus for practicing the amino acid analysis method of the present invention. The amino acid analyzer shown consists essentially of a buffer channel 1 extending from a feeder 2 for amino acid-containing samples and connected to an amino acid separating column 3, and an amino acid-containing eluate channel 4 extending from the column 3 and connected to a detector 5 equipped with a fluorophotometer. The eluate channel 4 is provided with a mixture reactor 7 for receiving o-phthalaldehyde and N-acetylcysteine and with a hypochlorite pre-reactor 6 disposed upstream from the the reactor 7. The mixture reactor 7 comprises an admixing channel 71 for supplying by a pump a borate buffer 72 having a pH of about 10 and containing o-phthalaldehyde and N-acetylcysteine, and a helical mixing tube. The reactor 7 is adapted to be maintained at a specified reaction temperature (usually 50° to 70° C.) by a heater.

The pre-reactor 6 comprises an injection channel 61 for supplying by a pump a borate buffer 62 containing sodium hypochlorite and having a pH of about 10, and a helical mixing tube and is similarly adapted to be maintained at a specified temperature. The drawing further shows a citric acid buffer 11 having a pH of 3.2 and a recorder 8. The illustrated apparatus is used for analyzing acidic amino acids only. For the analysis of various amino acids, a gradient apparatus is used which has a mobile phase varying stepwise or successively in pH and salt concentration as is the case with usual amino acid analyzers.

With the above apparatus, the buffer 11 is first supplied to the detector 5 through the channel 1, column 3 and channel 4. Subsequently an amino acid-containing sample is introduced from the feeder 2 into the channel 1 through a high-pressure six-way valve. The sample is then admitted into the column 3 and partitioned into component amino acids, which are led into the eluate channel 4. The separated amino acid phases are successivley fed to the pre-reactor 6, to which the hypochlorite is supplied. Consequently proline and like imino acid type secondary amino acids and other secondary amino acids are converted to primary amino acids in the pre-reactor 6. The separated phases are then led into the mixture reactor 7, to which o-phthalaldehyde and N-acetyl-cysteine are supplied. As a result, the primary amino acid components of these phases are converted to the corresponding condensed fluorescent heterocyclic derivatives according to the foregoing scheme, and the products are transferred to the detector 5, in which the intensities of fluorescence of the fluorescent compounds corresponding to the separated amino acids are measured. The recorder 8 records the measurements.

In this way, the sample containing amino acids including proline and like imino acids can be separated and analyzed with ease. The apparatus need not have the prereactor when not intended to analyze primary amino acids.

Figure 2:
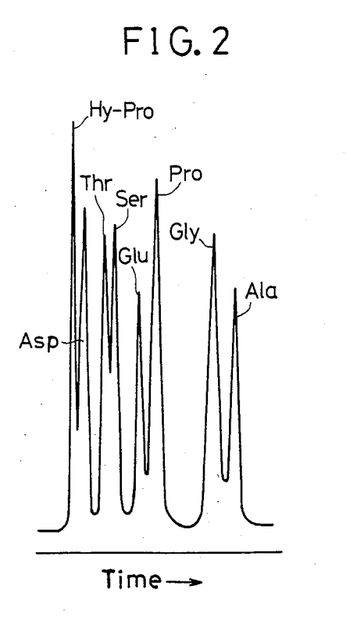
FIG. 2 is a graph showing an example of amino acid analysis chart obtained by the method of the invention.

FIG. 2 shows the results of amino acid analysis conducted with use of the above apparatus under the following conditions.

Measuring conditions

Buffer 11: 0.2N Na+ sodium citrate buffer (pH 3.2)
Column flow rate: 0.4 ml/min.
Column: ISC-07/S1504 (product of Shimadzu Seisakusho Ltd.)
Mixing tube:
  0.5 (diam.)×6 m for mixture reactor.
  0.5 (diam.)×12 cm for pre-reactor.
Buffer 72: Solution of 0.08% of OPA and 1 g of N-acetyl-L-cysteine in 500 ml of buffer* (flow rate: 0.2 ml/min).
Buffer 62: Solution of 0.4 ml of sodium hypochlorite ((0.1% Sol.) from Wako Junyaku Ltd.) in 500 ml of buffer* (flow rate: 0.2 ml/min).
Fluorescence measurement:
  Excitation wavelength 350 nm.
  Fluorescence wavelength: 450 nm.
Reaction temperature at mixture reactor and pre-reactor: 60° C.
Reaction time (passage time) in mixture reactor: 60 sec.
* $Na_2CO_3/H_3BO_3/K_2SO_4$ buffer having a pH of 10.

FIG. 2 reveals peaks detected for various amino acids, especially high peaks for proline (Pro) and hydroxyproline (Hy-Pro).

Figure 3:
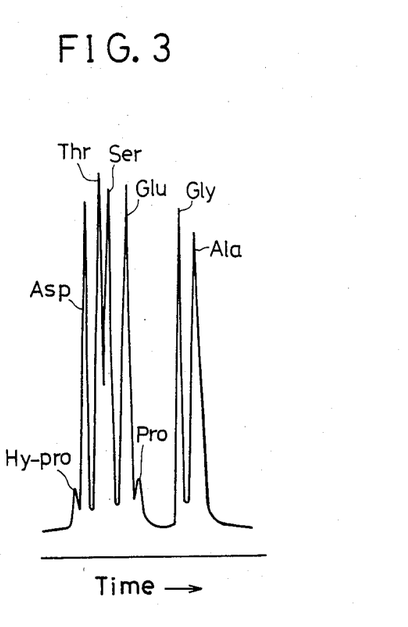
FIG. 3 is a graph showing an example of amino acid analysis chart obtained by the conventional method.

The same amino acid analysis procedure as above was repeated except that the N-acetyl-L-cysteine in the buffer 72 was replaced by 2-mercaptoethanol, i.e. conventional reaction reagent. FIG. 3, showing the results, reveals satisfactory peaks except very low peaks for Pro and Hy-Pro, indicating that the sensitivity achieved is as low as up to 1/10 the sensitivity of the method of the invention.

EXAMPLE 2

An 80 mg quantity of OPA was dissolved in 1 ml of methanol, and 1 g of N-acetyl-L-cysteine was added to the solution. The mixture was added to 100 ml of boric acid buffer having a pH of 10.4 to prepare a reaction reagent. To 1 ml portion of the reagent was added 2 mg of amino acid sample (D,L-alanine or D,L-valine), the mixture was shaken for 5 minutes, and 10 microliters of the mixture was placed through a high-pressure six-way valve into the column of a high-pressure liquid chromatographic device having a fluorophotometer as a detector. The sample was chromatographed under the following conditions.
Column: ERC-ODS-1272 (6 mm (diam.)×200 mm).
Mobile phase: Sodium acetate (pH 6.0)/methanol (65:35).
Flow rate: 1.0 ml/min.

Deteaction:
    Excitation wavelength 350 nm.
    Fluorescence wavelength 450 nm.
Column temperature: 50° C.

Figure 4:
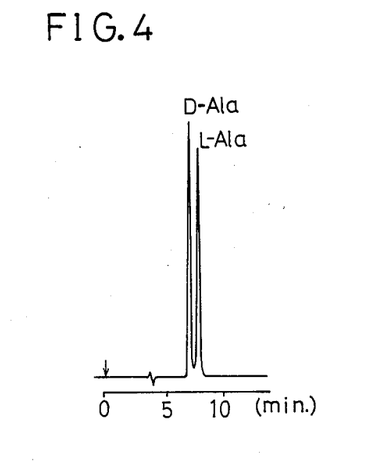
FIGS. 4 and 5 are other examples of amino acid optical resolution analysis charts obtained by the present method.
Figure 5:
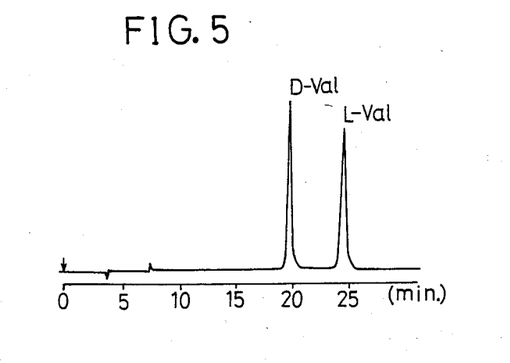

FIG. 4 shows the result achieved with use of D,L-alanine, and FIG. 5 the result obtained with D,L-valine.

Table 1 shows the retention time.

TABLE 1

| Amino acid | Retention time (min) |
|---|---|
| D-alanine | 7.5 |
| L-alanine | 8.1 |
| D-valine | 19.6 |
| L-valine | 24.4 |

Figure 6A:
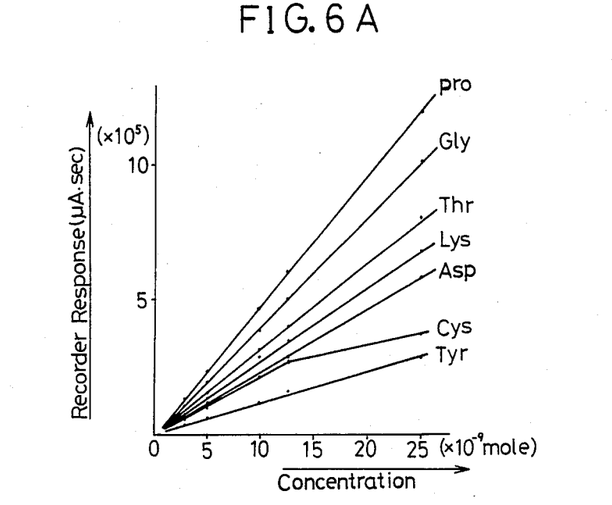
FIG. 6A and FIG. 6B are graphs showing the linearity of calibration curves obtained by the present method.
Figure 6B:
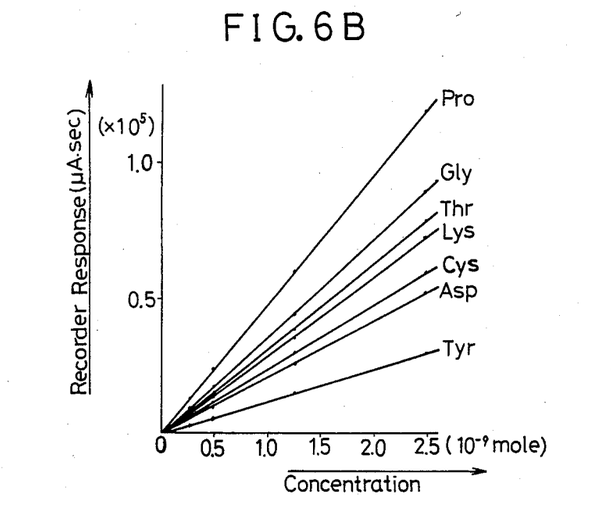

The high-concentration range is shown in FIG. 6A, and the lower concentration range in FIG. 6B. A satisfactory linear relationship is established for all the amino acids over a wide range. However, cysteine is shown to have a bent calibration line in the high concentration range.

Table 3 below shows the results obtained by checking the present method for repeated producibility of amino acid analyses. Each amino acid was analyzed at 500 picomoles 9 times with the listed results. The results are given in terms of C.V. value in the right-end column. The C.V. value was up to 1% for most of the amino acids, or up to 1.7% for all the amino acids.

TABLE 3

| | Reproducibility of Peak Area | | | | | | | | | | | |
|---|---|---|---|---|---|---|---|---|---|---|---|---|
| | 1 | 2 | 3 | 4 | 5 | 6 | 7 | 8 | 9 | M | SD | CV(%) |
| Asp | 1176 | 1184 | 1193 | 1216 | 1197 | 1190 | 1188 | 1202 | 1200 | 1194 | 10.9 | 0.9 |
| Thr | 1705 | 1709 | 1706 | 1743 | 1728 | 1718 | 1722 | 1729 | 1729 | 1721 | 12.0 | 0.7 |
| Ser | 1691 | 1710 | 1724 | 1740 | 1719 | 1715 | 1723 | 1737 | 1717 | 1720 | 13.7 | 0.8 |
| Glu | 1209 | 1243 | 1232 | 1267 | 1250 | 1253 | 1236 | 1236 | 1225 | 1239 | 15.9 | 1.3 |
| Pro | 2516 | 2575 | 2553 | 2596 | 2584 | 2563 | 2569 | 2567 | 2545 | 2563 | 22.0 | 0.9 |
| Gly | 2494 | 2505 | 2484 | 2525 | 2538 | 2501 | 2530 | 2532 | 2498 | 2512 | 18.1 | 0.7 |
| Ala | 1418 | 1433 | 1423 | 1425 | 1438 | 1430 | 1425 | 1418 | 1422 | 1426 | 6.4 | 0.4 |
| Cys | 1114 | 1110 | 1106 | 1096 | 1093 | 1061 | 1071 | 1064 | 1092 | 1090 | 18.7 | 1.7 |
| Val | 1654 | 1672 | 1651 | 1650 | 1650 | 1615 | 1635 | 1620 | 1659 | 1645 | 17.4 | 1.1 |
| Met | 982 | 989 | 988 | 1011 | 997 | 986 | 997 | 1005 | 994 | 994 | 8.8 | 0.9 |
| Ile | 1567 | 1568 | 1564 | 1581 | 1564 | 1573 | 1558 | 1576 | 1565 | 1568 | 6.7 | 0.4 |
| Leu | 1164 | 1154 | 1161 | 1164 | 1166 | 1173 | 1155 | 1163 | 1148 | 1161 | 7.0 | 0.6 |
| Tyr | 764 | 779 | 766 | 777 | 769 | 763 | 779 | 766 | 775 | 771 | 6.2 | 0.8 |
| Phe | 1434 | 1449 | 1448 | 1478 | 1461 | 1446 | 1463 | 1450 | 1474 | 1456 | 13.4 | 0.9 |
| His | 1827 | 1809 | 1817 | 1807 | 1809 | 1806 | 1797 | 1806 | 1803 | 1809 | 8.1 | 0.4 |
| Lys | 1554 | 1568 | 1545 | 1565 | 1577 | 1570 | 1575 | 1583 | 1570 | 1567 | 11.0 | 0.7 |
| Arg | 1216 | 1206 | 1182 | 1232 | 1207 | 1202 | 1216 | 1200 | 1217 | 1209 | 13.2 | 1.1 |

The results reveal that the method of the invention assures efficient optical resolution and high-sensitivity analyses.

EXAMPLE 3

An amino acid-containing sample was analyzed in the same manner as in Example 1 under the conditions of Table 2.

TABLE 2

Figure 9:
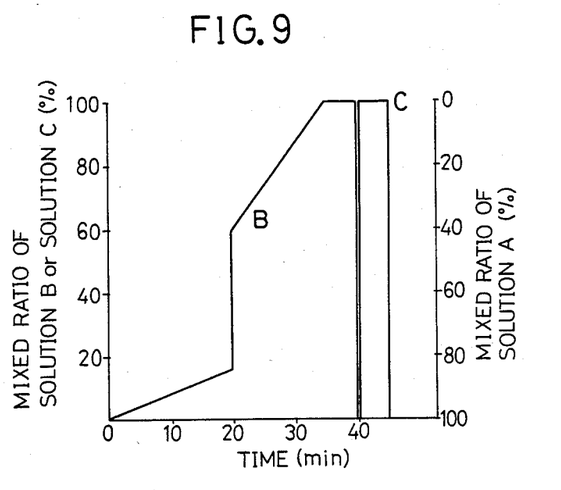
FIG. 9 is a graph showing a gradient profile of the mobile phase of Example 2.

| Column: | ISC-07/S1504 |
|---|---|
| Mobile phase: (gradient) | A. 0.2 N sodium citrate, pH 3.20 (7 w/w % in ethanol). |
| | B. 0.6 N sodium citrate, pH 10.0. |
| | C. 0.2 N sodium hydroxide (Gradient profile of the mobile phase is shown in FIG. 9) |
| Flow rate: | 0.3 ml/min. |
| Column temp.: | 55° C. |
| Detection: | RF-530, Ex 348 nm, Em 450 nm. |
| Reaction reagent: | A. 0.4 ml NaClO sol./1000 ml buffer.* |
| | B. 1.6 g OPA/15 ml ethanol, 4 ml 10% Brij-35 sol., 2 g N—AC—Cys, 980 ml buffer. |
| Reagent flow rate: | 0.2 ml/min each. |
| Reaction tube: | 20 cm length of former reaction tube and 2 mm length of latter reaction tube |

*pH buffer $Na_2CO_3$ (0.348 M), $H_3BO_3$ (0.216 M), $K_2SO_4$ (0.108 M)

The fluorescence detector was set to the same excitation and fluorescence wavelengths as in Example 1. The N-acetylcysteine used was a commercial product of special grade manufactured by Wako Junyaku Co., Ltd., as purified by recrystallization from hot water.

FIGS. 6A and 6B show the relationship between the amount of each amino acid applied to the column and the area of the chromatogram. The amount of amino acid was varied from 100 picomoles to 25 nanomoles.

EXAMPLE 4

Figure 7:
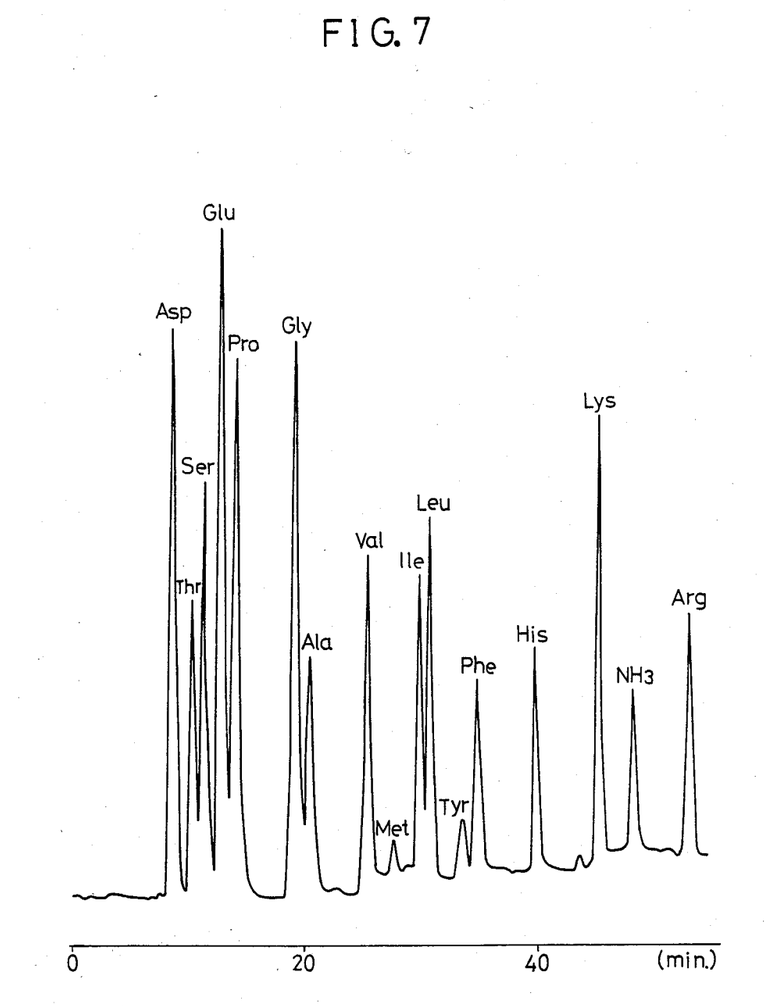
FIG. 7 and FIG. 8 are charts showing the results of amino acid analysis released from soy bean protein and a sample of amino acid mixture by the present method.

FIG. 7 shows the results obtained by analyzing a mixture of 17 amino acids. Soy bean protein was hydrolized with hydrochloric acid in the usual manner to prepare a mixture of amino acids, which was analyzed. The concentration of the mixture was so adjusted that about 500 picomoles of each amino acid was contained therein. Methionine, amino acid of soy bean protein, is also detected.

EXAMPLE 5

A sample containing 38 amino acids in mixture was subjected to amino acid analysis in the same manner as in Example 1 under the conditions of Table 4.

TABLE 4

Figure 10:
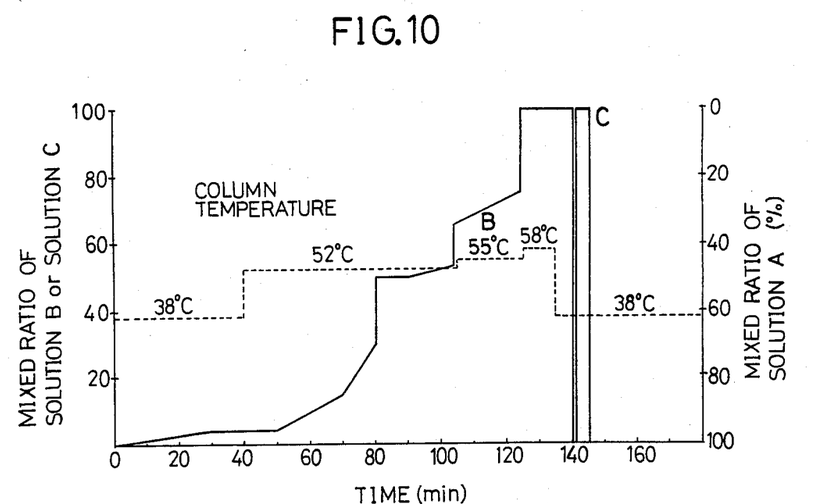
FIG. 10 is a graph showing a gradient profile of the mobile phase and the column temperature of Example 5.

| Column: | Lithium-ion type ISC-07/S1504 (styrenedivinylbenzene copolymer sulfonate of the lithium salt type). |
|---|---|
| Mobile phase: (gradient) | A. 0.15 N $Li^+$, lithium citrate, pH 2.60 (7 w/w % in methoxyethanol). |
| | B. 0.3 N $Li^+$, lithium citrate, pH 10.0. |
| | C. 0.2 N lithium citrate. |
| Reagent flow rate: | 0.4 ml/min. |
| Column temp.: | 40 to 58° C. (gradient). |

(Gradient profile of the mobile phase and the column temperature are shown in FIG. 10. The other conditions are the same as those listed in TABLE 2.)

Figure 8:
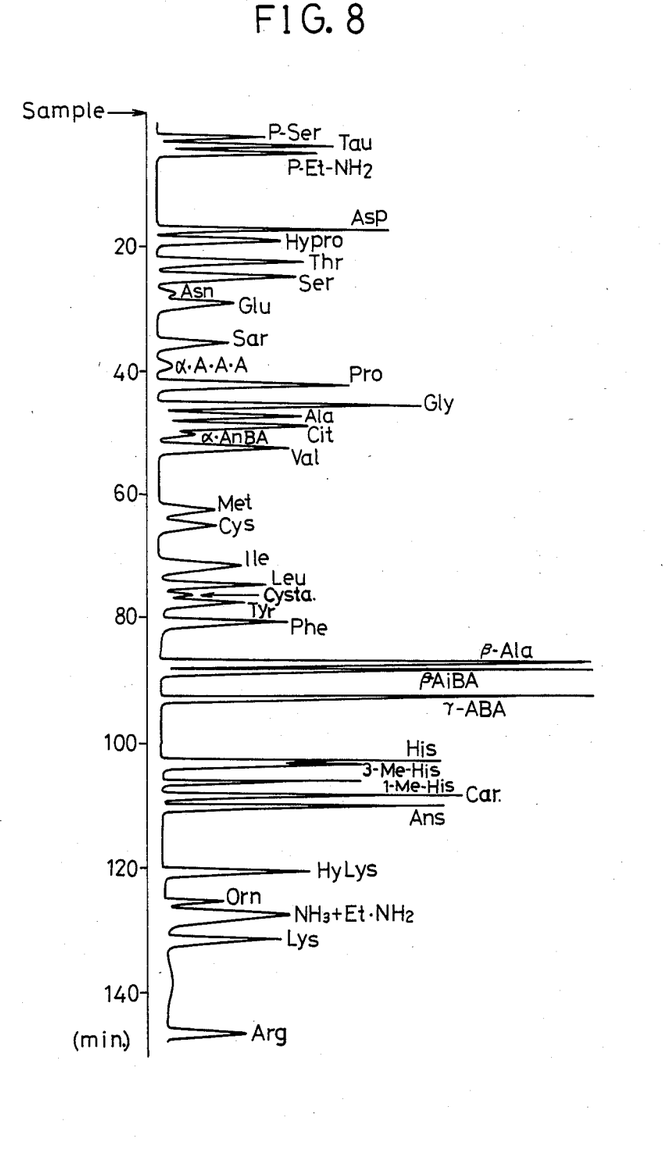

FIG. 8 shows the results.

Symbols in FIG. 8 stand for the following compounds.

| P—Ser | o-Phosphoserine |
|---|---|
| Tau | Taurine |
| P—Et-$NH_2$ | o-Phosphoethanolamine |
| Asn | Asparagine |

-continued

| | |
|---|---|
| α-AAA | α-Aminoadipic acid |
| Cit | Citrulline |
| α-AnBA | α-Amino-n-butyric acid |
| Cysta | Cystathionine |
| β-Ala | β-Alanine |
| β-AiBA | β-Amino-isobutyric acid |
| γ-ABA | γ-Aminobutyric acid |
| 3-Me-His | 3-Methylhistidine |
| 1-Me-His | 1-Methylhistidine |
| Car | Carnosine |
| Ans | Anserine |
| HyLys | Hydroxylysine |
| Orn | Ornithine |
| Et-NH₂ | Ethanolamine |

Thus, hydroxyproline (Hy-Pro) and sarcosine (Sar, methylglycine) can be detected also with high sensitivity.

What we claimed is:

1. A method of amino acid analysis which comprises (1) subjecting an amino acid-containing sample to liquid chromatography, thereby providing a separated amino acid phase, (2) treating the separated amino acid phase with an oxidizer to obtain an oxidized-amino acid phase, (3) treating said oxidized-amino acid phase with o-phthalaldehyde and N-acetyl-L-cysteine under an alkaline condition to yield a fluorescent compound, and (4) measuring intensity of fluorescence or absorbance of the fluorescent compound.

2. The method of claim 1 in which the amino acid-containing sample is one containing a primary amino acid.

3. The method of claim 1 wherein the amino acid-containing sample is a secondary amino acid-containing sample wherein said secondary amino acid is selected from the group consisting of proline and N-lower alkyl-substituted glycine.

4. The method of claim 1 in which step (3) is conducted in an alkaline buffer having a pH of 9 to 12.

5. The method of claim 4 in which the alkaline buffer is a borate type, carbonate type or borate-carbonate type buffer.

* * * * *